(12) United States Patent
Bosshard et al.

(10) Patent No.: US 10,667,853 B2
(45) Date of Patent: Jun. 2, 2020

(54) CABLE-LOCK FOR ORTHOPEDIC CABLES

(71) Applicant: Depuy Synthes Products, Inc., Raynham, MA (US)

(72) Inventors: Simon M. Bosshard, Zuchwil (CH); Andre Furrer, Zuchwil (CH); This Aebi, Zuchwil (CH)

(73) Assignee: SYNTHES GMBH, Raynham, MA (US)

(*) Notice: Subject to any disclaimer, the term of this patent is extended or adjusted under 35 U.S.C. 154(b) by 226 days.

(21) Appl. No.: 15/845,768

(22) Filed: Dec. 18, 2017

(65) Prior Publication Data

US 2019/0183553 A1    Jun. 20, 2019

(51) Int. Cl.
| | |
|---|---|
| A61B 17/56 | (2006.01) |
| A61B 17/58 | (2006.01) |
| A61B 17/80 | (2006.01) |
| A61F 2/30 | (2006.01) |
| A61B 17/88 | (2006.01) |
| A61F 2/08 | (2006.01) |
| A61B 17/84 | (2006.01) |
| A61B 17/82 | (2006.01) |

(52) U.S. Cl.
CPC ......... *A61B 17/8861* (2013.01); *A61B 17/82* (2013.01); *A61B 17/842* (2013.01); *A61B 17/8869* (2013.01); *A61F 2/0811* (2013.01); *A61F 2002/087* (2013.01); *A61F 2002/0817* (2013.01); *A61F 2002/0876* (2013.01)

(58) Field of Classification Search
CPC combination set(s) only.
See application file for complete search history.

(56) References Cited

U.S. PATENT DOCUMENTS

| | | | |
|---|---|---|---|
| 3,994,521 A | 11/1976 | Gompel | |
| 5,935,130 A * | 8/1999 | Kilpela | A61B 17/8869 606/103 |
| 6,668,427 B2 | 12/2003 | Bulanda et al. | |
| 2004/0016085 A1 | 1/2004 | Caveney | |

FOREIGN PATENT DOCUMENTS

KR    10-2014-0022643    2/2014

* cited by examiner

*Primary Examiner* — Sameh R Boles
(74) *Attorney, Agent, or Firm* — Kramer Amado, P.C.

(57) ABSTRACT

A cable-lock device includes a housing, having a length-axis between a distal end for accepting a cable and a proximal end for exiting a cable, including a first bore parallel to the length-axis of the housing and configured to allow passage of the cable, a second bore off-center from and parallel to the first bore including a tappet axially displaceable in the second bore and parallel to the length axis of the housing, and a third bore oblique to the first bore which intersects with the first bore including a locking roller axially displaceable in the third bore with a predetermined angulation to the length-axis of the housing, a resilient structure which exerts a force on the locking roller in the direction of the intersection of the first bore and the third bore, and a fastener unit at the proximal end of the third bore.

59 Claims, 6 Drawing Sheets

CABLE-LOCK FOR ORTHOPEDIC CABLES

TECHNICAL FIELD

This disclosure relates generally to a multiple-use cable-lock for transmitting tensile forces onto an orthopedic cable in order to grasp and lock the cable.

BACKGROUND

During certain surgical procedures, specifically during orthopedic surgical procedures, it is a common requirement to anchor two or more elements together, such as pieces of a bone, two or more bones, or a combination of soft tissue and bone. This has been accomplished by a number of devices, such as bone bolts that penetrate two pieces of bone and use a nut to draw the segments together, bone screws and interconnecting plates, wires circling at least two pieces of bone, or sutures into the tissue.

Often such devices require a relatively large access opening through surrounding and/or covering tissue to implant and operate the anchoring devices. The enlarged access opening may increase patient pain and lengthen recovery time for the patient. Further, in some operation locations, it is difficult and impractical to make these large access openings to reach the appropriate site because of surrounding joints and blood vessels.

Cerclage systems provide an alternative to implants that must penetrate the bone to achieve fixation. These systems rely on passing a cable around two segments of bone and then tensioning, crimping and cutting the cable to squeeze the bone segments together.

Previous tensioning tools employed grasping and locking mechanisms, which, under high tension, would cause fraying and kinking in the cables. There is a need for cable grasping and locking devices that do not damage the cable.

SUMMARY OF EXEMPLARY EMBODIMENTS

A brief summary of various embodiments is presented below. Embodiments address the need to grasp and lock cables in a cable lock device without damaging the cable.

In order to overcome these and other shortcomings of the prior art and in light of the need for a cable-lock device for grasping and locking cables, a brief summary of various exemplary embodiments is presented. Some simplifications and omissions may be made in the following summary, which is intended to highlight and introduce some aspects of the various exemplary embodiments, but not to limit the scope of the invention. Detailed descriptions of a preferred exemplary embodiment adequate to allow those of ordinary skill in the art to make and use the inventive concepts will follow in later sections.

Various embodiments relate to a cable-lock device for grasping and locking a cable that includes: a housing, having a length-axis between a distal end for accepting a cable and a proximal end for exiting a cable, including a first bore parallel to the length-axis of the housing and configured to allow passage of the cable, a second bore off-center from and parallel to the first bore including a tappet axially displaceable in the second bore and parallel to the length axis of the housing and a third bore oblique to the first bore at a predetermined angulation to the length-axis of the housing, which intersects with the first bore, wherein the third bore includes a locking roller axially displaceable in the third bore, a resilient structure which exerts a force on the locking roller in the direction of the intersection of the first bore and the third bore, and a fastener unit at the proximal end of the third bore.

Various embodiments relate to a cable-lock device for grasping and locking a cable that includes: a housing, having a length-axis between a distal end for accepting a cable and a proximal end for exiting a cable, including a first bore parallel to the length-axis of the housing and configured to allow passage of the cable, a second bore off-center from and parallel to the first bore including a tappet axially displaceable in the second bore and parallel to the length axis of the housing and a third bore oblique to the first bore at a predetermined angulation to the length-axis of the housing, which intersects with the first bore, wherein the third bore includes a locking roller axially displaceable in the third bore, a resilient structure which exerts a force on the locking roller in the direction of the intersection of the first bore and the third bore, and a fastener unit at the proximal end of the third bore. The device is configured to grasp and lock the cable through friction between the locking roller and the cable, friction between the locking roller and the housing, and friction between the housing and the cable.

Various embodiments relate to a cable-lock device for grasping and locking a cable that includes: a housing, having a length-axis between a distal end for accepting a cable and a proximal end for exiting a cable, including a first bore parallel to the length-axis of the housing and configured to allow passage of the cable, a second bore off-center from and parallel to the first bore including a tappet axially displaceable in the second bore and parallel to the length axis of the housing and a third bore oblique to the first bore at a predetermined angulation to the length-axis of the housing, which intersects with the first bore, wherein the third bore includes a locking roller axially displaceable in the third bore, a resilient structure which exerts a force on the locking roller in the direction of the intersection of the first bore and the third bore, and a fastener unit at the proximal end of the third bore. The device is configured to grasp and lock the cable through movement trajectories between the cable and the locking roller forming a pointed angle, leading to a movement of the locking roller relative to the housing, wherein the locking roller moves together with the cable along its length-axis and against its cross-axis.

Various embodiments recite a cable-lock device including, a housing including a first bore configured to allow passage of a cable, a tappet axially displaceable in a second bore, a locking roller axially displaceable in a third bore with a predetermined angulation to the length-axis of the housing, an adapter in contact with the locking roller at a distal end of the adapter, a resilient structure in contact with the adapter at a proximal end of the adapter and a fastener unit securing the resilient structure, adapter, locking roller and tappet from dislocation.

In various embodiments, the resilient structure pushes the adapter together with the locking roller and the tappet in a distal direction until the proximal end of the tappet is stopped by the proximal front-end of the second bore. In one embodiment, the locking roller covers the first bore along the length-axis of the housing by approximately half of its diameter.

In various embodiments, the locking roller initially at least partially obscures the first bore. A cable, inserted through the distal opening of the first bore pushes the locking roller along an angulated third bore to the proximal end. In one embodiment, as soon as the locking roller does not cover the first bore, the cable passes the locking roller and can be pushed further until it leaves the housing at its proximal end. In such embodiment, free movement of the cable from distal end to proximal end of the device is always possible.

In various embodiments, when the cable is pulled in the distal direction, the locking roller is pressed onto the cable and the gripping force on the cable is increased. In one embodiment, the friction and the spherical shape of the locking roller support this effect. In such embodiment, free movement of the cable from a proximal to a distal direction through the first bore of the housing is not possible and restricted due to the presence of the locking roller.

In various embodiments, the cable lock device is configured to accommodate cables having different diameters.

In various embodiments, the cable lock device is configured to be removably attached to another cable handling or tensioning device.

BRIEF DESCRIPTION OF THE DRAWINGS

The accompanying figures, where like reference numerals refer to identical or functionally similar elements throughout the separate views, together with the detailed description below, are incorporated in and form part of the specification, and serve to further illustrate embodiments of concepts that include the claimed invention, and explain various principles and advantages of those embodiments.

These and other more detailed and specific features of the invention are more fully disclosed in the following specification, reference being had to the accompanying drawings, in which.

Figure 1A:
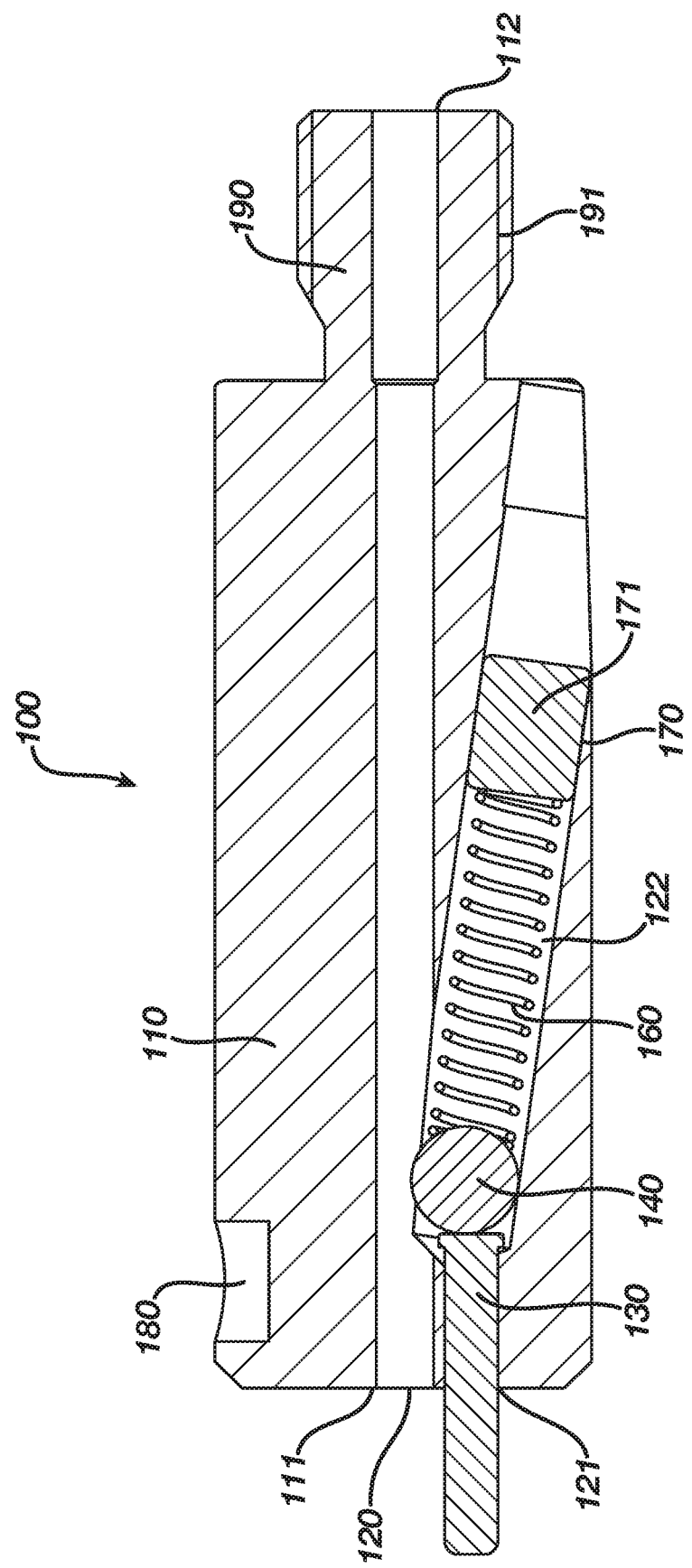
FIG. 1A illustrates a cross-sectional side view of one embodiment of a cable-lock device.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the invention.

The apparatus and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION OF THE INVENTION

It should be understood that the figures are merely schematic and are not drawn to scale. It should also be understood that the same reference numerals are used throughout the figures to indicate the same or similar parts.

The descriptions and drawings illustrate the principles of various example embodiments. It will thus be appreciated that those skilled in the art will be able to devise various arrangements that, although not explicitly described or shown herein, embody the principles of the invention and are included within its scope. Furthermore, all examples recited herein are principally intended expressly to be for pedagogical purposes to aid the reader in understanding the principles of the invention and the concepts contributed by the inventor(s) to furthering the art, and are to be construed as being without limitation to such specifically recited examples and conditions. Additionally, the term, "or," as used herein, refers to a non-exclusive or (i.e., and/or), unless otherwise indicated (e.g., "or else" or "or in the alternative"). Also, the various embodiments described herein are not necessarily mutually exclusive, as some embodiments can be combined with one or more other embodiments to form new embodiments. Descriptors such as "first," "second," "third," etc., are not meant to limit the order of elements discussed, are used to distinguish one element from the next, and are generally interchangeable.

Embodiments of a cable-lock device 100 for grasping and locking cables are described below. The cable-lock device 100 may be used for grasping and locking cables having a diameter of up to 2.0 mm, more specifically 1.0 mm, 1.3 mm, 1.5 mm, 1.7 mm, 1.8 mm and 2.0 mm, independent of cable material and strand type. In some embodiments, suitable cable materials include stainless steel or cobalt-chrome materials. The cable-lock device 100 enables grasping and locking of the cable without any fraying or kinking of the cable. The cable-lock device 100 may be attached to any other cable-handling or tensioning instrument (not shown) to grasp and lock the cable to the instrument to lower manufacturing costs and complexity.

In some embodiments, multiple cable lock devices may be attached together to accommodate one cable. The multiple cable lock devices may include multiple housings, multiple tappets, multiple locking rollers, multiple adapters, multiple resilient structures, and multiple fastener units, to accommodate one cable. The multiple cable lock devices may also include multiple oblique third bores with predetermined angulations to the length axes of the multiple housings.

The cable-lock device 100 may allow for self-retaining grasping and locking of cables as well as active, forced unlocking of cables. In some embodiments, the cable-lock device 100 may additionally allow for in-line grasping and locking of cables made from different materials, with different diameters, and with different strand types without any radial deflection of the cable.

The cable-lock device 100 may allow grasping and locking of the cable through the use of a locking roller 140, utilizing the friction between the locking roller 140 and the cable, the friction between the locking roller 140 and the housing 110 and the friction between the housing 110 and the cable. In some embodiments, the cable-lock device 100 allows for locking and grasping of the cable through movement trajectories between the cable and the locking roller 140 forming a pointed angle, leading to a movement of the locking roller 140 relative to the housing 110, wherein the locking roller 140 moves together with the cable along its length-axis and against its cross-axis. In some embodiments, a small elastic deformation in the cable is introduced as the locking roller 140 presses onto the cable. This introduced form-fit additionally supports the grasping and locking of the cable.

The cable-lock device 100 allows for in-line grasping and locking of cables through the following self-controlled sequence: reset position→cable grasping→cable locking→relief of cable locking→relief of cable grasping→reset position. The cable-lock device 100 in the reset position allows for free movement of the cable in a distal and proximal direction. The cable-lock device 100 in its cable grasping state allows for a movement of the cable only in a proximal direction, to allow a pre-tensioning of the cable by pulling directly on the cable by hand in a proximal direction. The cable-lock device 100 in its cable locking state allows for a movement of the cable only in a proximal direction, if the pulling force in the proximal direction on the cable, introduced by hand, is higher than the actual tensioning force in the distal direction.

The grasping of the cable begins as soon as the locking roller 140 is in contact with the cable and still in contact with the tappet 130. This may occur as soon as the elastic resilient structure 160 expands, pushing the locking roller 140 together with the tappet 130 in a distal direction. The locking of the cable begins as soon as the locking roller 140 is in contact with the cable only and is able to move further in a distal direction together with the cable. This may occur as soon as the tappet 130 is not in contact with the locking roller 140 and thus, does not restrict the movement of the locking roller 140 in a distal direction.

The maximum pulling force transmitted by the device 100 onto the cable is defined by the maximum tensile force of the cable. The locking roller 140, when in contact with the cable and in contact with the tappet 130, maintains a tensile force on the cable from between 0 N to about the maximum tensile force of the cable. In some embodiments, the locking roller 140, when in contact with the cable and in contact with the tappet 130 allows for a controlled dragging and deceleration of the cable when the cable is moved from a proximal to a distal direction. The tensile force on the cable may decrease over time. In some embodiments, the locking roller 140 introduces a constant contact force onto the cable, introduced through the resilient structure 160, to control the diameter of the cable when the cable is moved from a proximal to a distal direction.

The relief of cable locking begins as soon as the tappet 130 is in contact with the locking roller 140 and introduces a force onto the locking roller 140 in a proximal direction. The relief of cable grasping begins when the locking roller 140 moves in a proximal direction and loses contact with the cable. This may occur when the tappet 130 is in contact with the locking roller 140, pushing the locking roller 140 and compressing the resilient structure 160 in a proximal direction. The final reset position is reached through an axial displacement of the tappet 130 in a proximal direction, including the movement of the locking roller 140 and the compression of the resilient structure 160 in a proximal direction.

FIG. 1A illustrates a cross-sectional side view of the cable-lock device 100, wherein the device 100 is in a locked position. The cable-lock device 100 includes a housing 110 including a first bore 120 parallel to the length axis of the housing 110, defined by a distal end 111 for accepting the cable and a proximal end 112 through which the cable exits. The housing 110 additionally includes a second bore 121, parallel to the length axis of the housing 110 and a third bore 122 oblique to the first bore 120. The second bore 121 includes a tappet 130 positioned therein which also runs parallel to the length-axis of the housing 110. The third bore 122 includes a locking roller 140 and a resilient structure 160. The resilient structure 160, locking roller 140 and tappet 130 are secured to the housing 110 by a fastener unit 170. The fastener unit 170 in the embodiment of FIG. 1A is in the form of a welded block 171. The housing 110 also includes an indentation 180 configured to accept an additional part (not shown) to block rotation of the device 100. The housing 110 further includes a connector 190 at a proximal end for attachment to various cable handling or tensioning devices (not shown). In some embodiments, the locking roller 140 may be in the form of a ball or a rounded cylinder. In some embodiments, the resilient structure 160 may be a spring or other device for applying a force to the locking roller 140 in the direction of the intersection of the first bore 120 and the third bore 122. In some embodiments, the connector 190 may include optional threading 191.

Figure 1B:
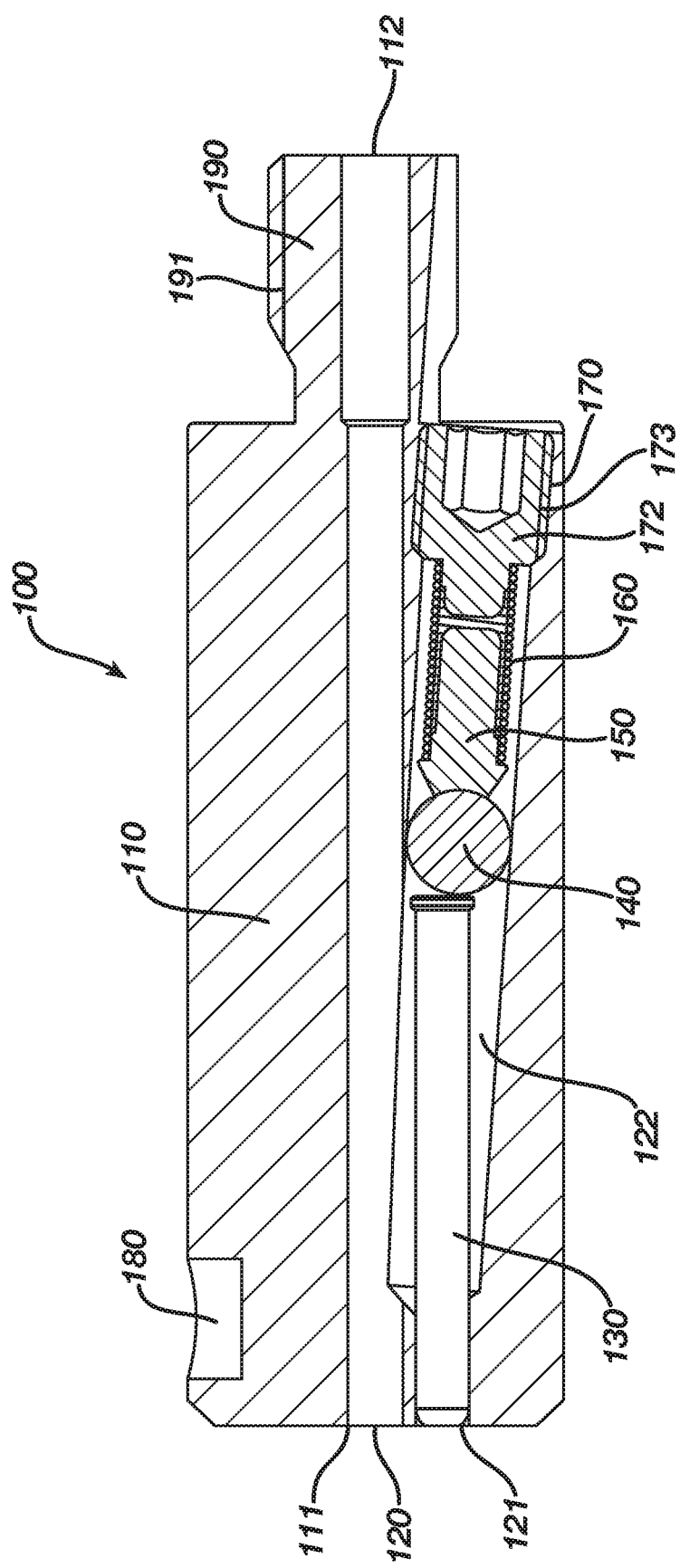
FIG. 1B illustrates a cross-sectional side view of another embodiment of a cable-lock device.

FIG. 1B illustrates a cross-sectional side view of another embodiment of the cable-lock device 100 for in-line grasping and locking of a cable, wherein the device 100 is in a reset position. The cable-lock device 100 includes a housing 110 including a first bore 120 parallel to the length axis of the housing 110, defined by a distal end 111 for accepting the cable and a proximal end 112 through which the cable exits. The housing 110 additionally includes a second bore 121, parallel to the length axis of the housing 110 and a third bore 122 oblique to the first bore 120. The second bore 121 includes a tappet 130 positioned therein which also runs parallel to the length-axis of the housing 110. The third bore 122 includes a locking roller 140, an adapter 150 in contact with the locking roller 140 at a distal end of the adapter 150, a resilient structure 160 in contact with the adapter 150 at a proximal end of the adapter 150 and a fastener unit 170 that secures the resilient structure 160, the adapter 150, the locking roller 140 and the tappet 130 from dislocation from the housing 110. The fastener unit 170 in the embodiment of FIG. 1B is in the form of a removable screw 172. In this embodiment, the resilient structure 160 is configured to fit around a cylindrical barrel 352 (not shown) of the adapter 150 and around a coupling 471 (not shown) of the fastener unit 170. The fastener unit 170 may include optional threading 173. The housing 110 further includes a connector 190 at a proximal end for attachment to various cable handling or tensioning devices (not shown). In some embodiments, the connector 190 may include optional threading 191.

In FIGS. 1A-B, the locking roller 140 is axially displaceable in the third bore 122 with a predetermined angulation to the length-axis of the housing 110. In some embodiments, the predetermined angulation ranges from greater than 0 to about 20 degrees, preferably from greater than 0 to about 10 degrees. In some embodiments, the locking roller 140 may have a diameter between about 3 mm to about 5 mm, more preferably about 4 mm. In some embodiments, the resilient structure 160 may have a diameter between about 2 mm to about 4 mm, more preferably about 3 mm.

Figure 1C:
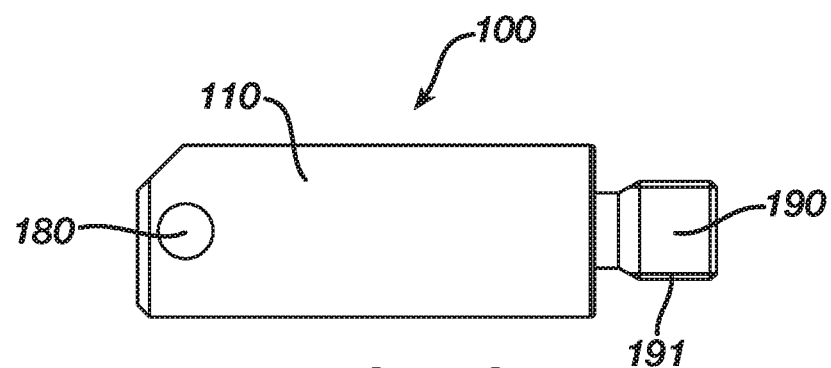
FIG. 1C illustrates a top view of one embodiment of the housing of a cable-lock device.
Figure 1D:
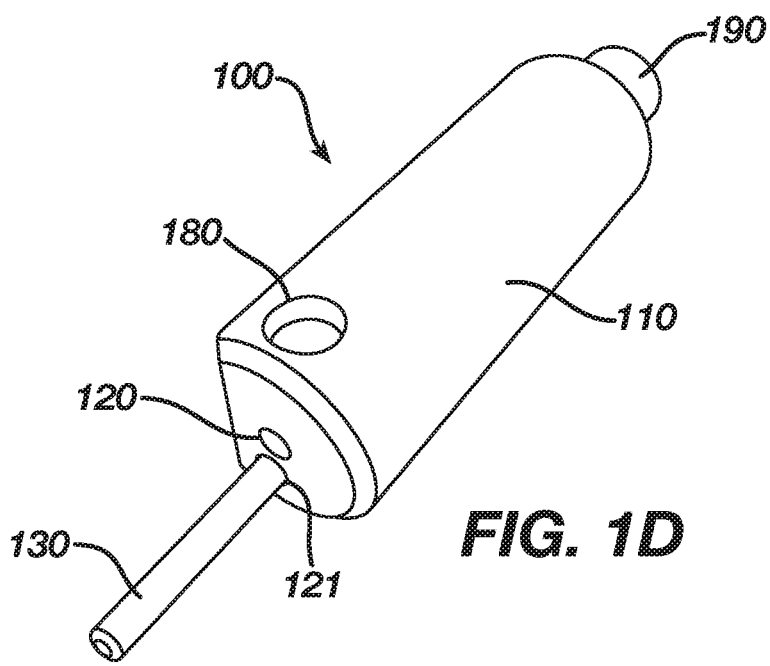
FIG. 1D illustrates a perspective view of one embodiment of a cable-lock device.
Figure 1E:
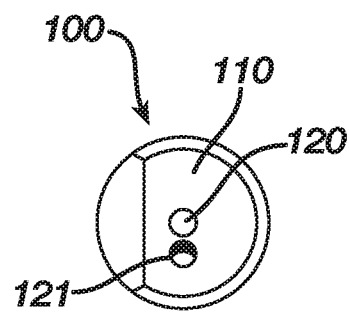
FIG. 1E illustrates a distal view of one embodiment of the housing of a cable-lock device.

FIG. 1C illustrates a top view of the housing 110, showing in more detail the indentation 180 contained on the housing 110 that is configured to accept an additional part (not shown) to block rotation of the cable-lock device 100. FIG. 1D illustrates a perspective view of the cable-lock device 100 in a locked position showing in more detail the positioning of the tappet 130 in the second bore 121. FIG. 1E illustrates a distal view of the housing 110, showing in more detail the first bore 120 that is configured to allow passage of a cable and the second bore 121 positioned off-center from the first bore 120.

Figure 2A:
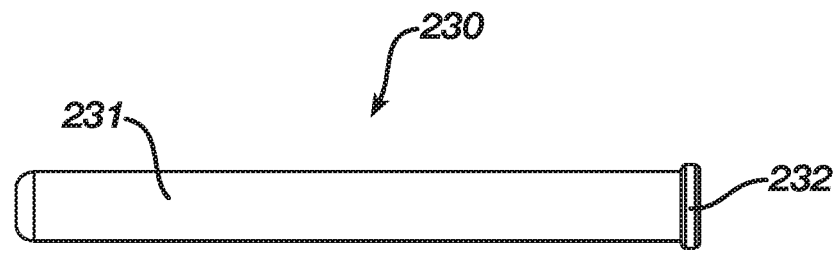
FIGS. 2A and 2B illustrate a side view and perspective view of the tappet described in FIGS. 1A and 1B.
Figure 2B:
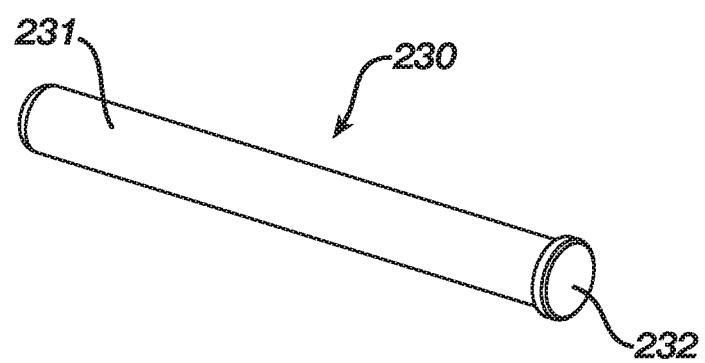

FIGS. 2A and 2B illustrate a side view and perspective view of the tappet 230. The tappet 230 may be configured to include an elongated cylinder 231 configured to pass through the second bore 121 in a proximal and distal direction. The tappet 230 may include an end piece 232 on the proximal end of the elongated cylinder 231 having a larger circumference and diameter than the elongated cylinder 231. The end piece 232 is configured to maintain the tappet 230 in the second bore 121 and prevent exit of the tappet 230 from the distal end of the housing 110 through the second bore 121.

Figure 3A:
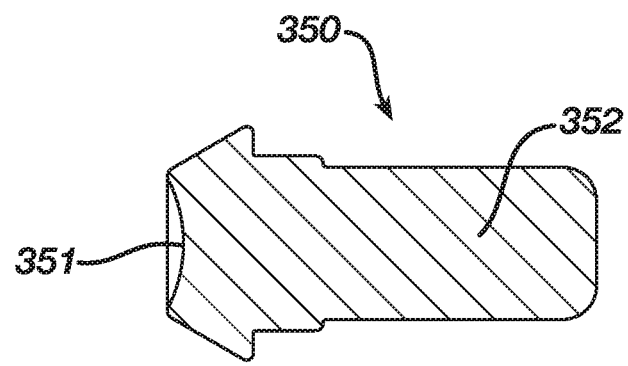
FIGS. 3A and 3B illustrate a cross-sectional side view and perspective view of the adapter described in FIG. 1B.
Figure 3B:
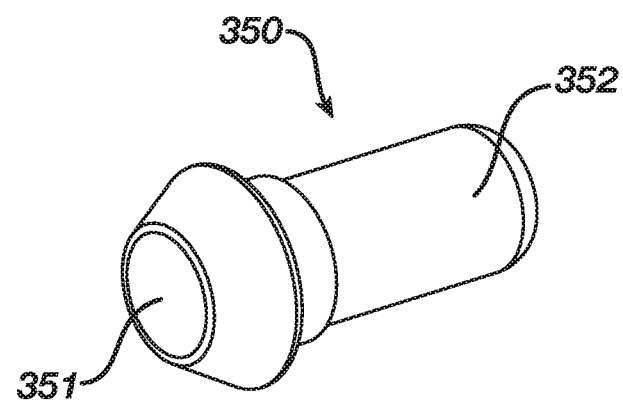

FIGS. 3A and 3B illustrate a cross-sectional side view and perspective view, respectively, of the adapter 350. The adapter 350 may be configured to include a concave depression 351 on its distal end to accommodate the locking roller 140 and a cylindrical barrel 352 on its proximal end. In one embodiment, the resilient structure 160 may be configured to fit around the cylindrical barrel 352 of the adapter 350.

Figure 4A:
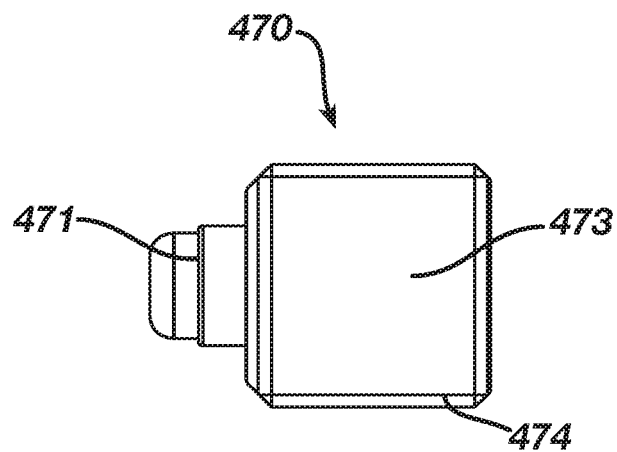
FIGS. 4A and 4B illustrate a side view and proximal view of the fastener unit described in FIG. 1B.
Figure 4B:
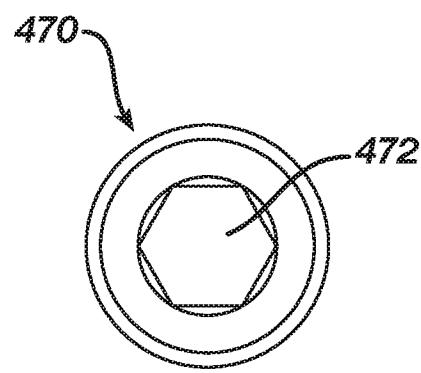

FIGS. 4A-B illustrate a side view and proximal view of an embodiment of a fastener unit 470. The fastener unit 470 may include a set screw 473 with an adapted distal end to a coupling 471, having a normal screw recess 472 on the proximal end. The fastener unit may include optional threading 474.

The cable-lock device 100 described in FIGS. 1-4 may be operated by inserting a cable through the distal end 111 of the first bore 120. As substantially shown in FIG. 1A, in the locking position, the resilient structure 160 pushes the locking roller 140 so that the locking roller 140 at least partially obscures the first bore 120. When inserted through the distal end 111 of the first bore 120, the cable pushes the locking roller 140 along the angulated third bore 122 to the proximal end of the device. As soon as the locking roller 140 does not cover the first bore 120, the cable passes the locking roller 140 and can be pushed further until it leaves the housing 110 at its proximal end. If the inserted cable is pulled in a distal direction, the locking roller 140 is moved, with support by the force of the resilient structure 160, together with the cable. When the cable is moved in a distal direction, the locking roller 140 is pressed onto the cable and the gripping force of the locking roller 140 is increased as the cable is moved further in a distal direction. The friction and the spherical shape of the locking roller 140 support this effect. In this position, free movement of the cable from the proximal to the distal end of the device 100 through the first bore 120 of the housing 110 is never possible and restricted through the locking roller 140.

As shown in FIG. 1B, the cable may be unlocked by pushing the tappet 130 in a proximal direction towards the direction of the locking roller 140. The tappet 130 contacts the locking roller 140 and introduces a force onto the locking roller 140, in order to initiate relief of the cable locking. Once the locking roller 140 moves in a proximal direction and loses contact with the cable, the cable is free to be removed from the device 100 in either the distal or proximal direction.

Accordingly, it is to be understood that the above description is intended to be illustrative and not restrictive. Many embodiments and applications other than the examples provided would be apparent upon reading the above description. The scope should be determined, not with reference to the above description or Abstract below, but should instead be determined with reference to the appended claims, along with the full scope of equivalents to which such claims are entitled. It is anticipated and intended that future developments will occur in the technologies discussed herein, and that the disclosed systems and methods will be incorporated into such future embodiments. In sum, it should be understood that the application is capable of modification and variation.

The benefits, advantages, solutions to problems, and any element(s) that may cause any benefit, advantage, or solution to occur or become more pronounced are not to be construed as a critical, required, or essential features or elements of any or all the claims. The invention is defined solely by the appended claims including any amendments made during the pendency of this application and all equivalents of those claims as issued.

Moreover in this document, relational terms such as first and second, top and bottom, and the like may be used solely to distinguish one entity or action from another entity or action without necessarily requiring or implying any actual such relationship or order between such entities or actions. The terms "comprises," "comprising," "has," "having," "includes," "including," "contains," "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a," "has . . . a," "includes . . . a," or "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially," "essentially," "approximately," "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus the following claims are hereby incorporated into the Detailed Description, with each claim standing on its own as a separately claimed subject matter.

What is claimed is:
1. A cable lock device comprising:
a housing comprising a length-axis between a distal end for accepting a cable and a proximal end for exiting a cable, comprising:
a first bore parallel to the length-axis of the housing and configured to allow passage of the cable;
a second bore off-center from and parallel to the first bore comprising:
a tappet axially displaceable in the second bore and parallel to the length axis of the housing; and a third bore oblique to the first bore at a predetermined angulation to the length axis of the housing, wherein the third bore intersects the first bore comprising:
a locking roller axially displaceable in the third bore,
a resilient structure which exerts a force on the locking roller in the direction of the intersection of the first bore and the third bore, and
a fastener unit at the proximal end of the third bore.

2. The device of claim 1, further comprising an adapter in contact with the locking roller at a distal end of the adapter and the resilient structure at a proximal end of the adapter.

3. The device of claim 1, wherein the locking roller comprises a ball.

4. The device of claim 1, wherein the locking roller comprises a rounded cylinder.

5. The device of claim 1, wherein the resilient structure comprises a spring.

6. The device of claim 1, wherein the fastener unit comprises a welded block.

7. The device of claim 1, wherein the fastener unit comprises a removable screw.

8. The device of claim 1, wherein the predetermined angulation of the third bore to the length axis of the housing is greater than 0° to about 20°.

9. The device of claim 8, wherein the predetermined angulation of the third bore to the length axis of the housing is about 10°.

10. The device of claim 1, wherein the locking roller is configured to move together with the cable along its length-axis and against its cross-axis.

11. The device of claim 1, wherein movement of the locking roller together with the cable allows for self-retaining grasping and locking of the cable.

12. The device of claim 11, wherein friction between the locking roller, the cable and the housing grasps and locks the cable without radial deflection of the cable.

13. The device of claim 12, wherein the cable is actively unlocked through introduction of a force onto the locking roller in a proximal direction.

14. The device of claim 13, wherein the force is initiated by the tappet, wherein the tappet pushes the locking roller against the resilient structure in a proximal direction.

15. The device of claim 11, wherein the locking roller is in contact with the cable and in contact with the tappet to allow for a controlled dragging and deceleration of the cable when the cable is moved from a proximal to a distal direction.

16. The device of claim 11, wherein the locking roller is in contact with the cable and in contact with the tappet to maintain a tensile force on the cable between 0 N to about the maximum tensile force of the cable.

17. The device of claim 16, wherein the tensile force on the cable decreases over time.

18. The device of claim 11, wherein the locking roller introduces a constant contact force onto the cable, introduced through the resilient structure, to control the diameter of the cable when the cable is moved from a proximal to a distal direction.

19. The device of claim 1, wherein the amount of force exerted on the locking roller by the cable is greater than 0 N to about the maximum tensile force of the cable.

20. The device of claim 1, wherein the cable has a diameter of up to 2.0 mm.

21. A cable lock device comprising:
a housing comprising a length-axis between a distal end for accepting a cable and a proximal end for exiting a cable, comprising:
a first bore parallel to the length-axis of the housing and configured to allow passage of the cable;
a second bore off-center from and parallel to the first bore comprising:
a tappet axially displaceable in the second bore and parallel to the length axis of the housing; and
a third bore oblique to the first bore at a predetermined angulation to the length axis of the housing, wherein the third bore intersects the first bore comprising:
a locking roller axially displaceable in the third bore,
a resilient structure which exerts a force on the locking roller in the direction of the intersection of the first bore and the third bore, and
a fastener unit at the proximal end of the third bore;
wherein the device is configured to grasp and lock the cable through friction between the locking roller and the cable, friction between the locking roller and the housing, and friction between the housing and the cable.

22. The device of claim 21, further comprising an adapter in contact with the locking roller at a distal end of the adapter and the resilient structure at a proximal end of the adapter.

23. The device of claim 21, wherein the locking roller comprises a ball.

24. The device of claim 21, wherein the locking roller comprises a rounded cylinder.

25. The device of claim 21, wherein the resilient structure comprises a spring.

26. The device of claim 21, wherein the fastener unit comprises a welded block.

27. The device of claim 21, wherein the fastener unit comprises a removable screw.

28. The device of claim 21, wherein the predetermined angulation of the third bore to the length axis of the housing is greater than 0° to about 20°.

29. The device of claim 28, wherein the predetermined angulation of the third bore to the length axis of the housing is about 10°.

30. The device of claim 21, wherein the locking roller is configured to move together with the cable along its length-axis and against its cross-axis.

31. The device of claim 21, wherein movement of the locking roller together with the cable allows for self-retaining grasping and locking of the cable.

32. The device of claim 31, wherein the locking roller is in contact with the cable and in contact with the tappet to allow for a controlled dragging and deceleration of the cable when the cable is moved from a proximal to a distal direction.

33. The device of claim 31, wherein the locking roller is in contact with the cable and in contact with the tappet to maintain a tensile force on the cable between 0 N to about the maximum tensile force of the cable.

34. The device of claim 33, wherein the tensile force on the cable decreases over time.

35. The device of claim 31, wherein the locking roller introduces a constant contact force onto the cable, introduced through the resilient structure, to control the diameter of the cable when the cable is moved from a proximal to a distal direction.

36. The device of claim 31, wherein friction between the locking roller, the cable and the housing grasps and locks the cable without radial deflection of the cable.

37. The device of claim 36, wherein the cable is actively unlocked through introduction of a force onto the locking roller in a proximal direction.

38. The device of claim 37, wherein the force is initiated by the tappet, wherein the tappet pushes the locking roller against the resilient structure in a proximal direction.

39. The device of claim 21, wherein the amount of force exerted on the locking roller and the device by the cable is greater than 0 N to about the maximum tensile force of the cable.

40. The device of claim 21, wherein the cable has a diameter of up to 2.0 mm.

41. A cable lock device comprising:
a housing comprising a length-axis between a distal end for accepting a cable and a proximal end for exiting a cable, comprising:
a first bore parallel to the length-axis of the housing and configured to allow passage of the cable;
a second bore off-center from and parallel to the first bore comprising:
a tappet axially displaceable in the second bore and parallel to the length axis of the housing; and
a third bore oblique to the first bore at a predetermined angulation to the length axis of the housing, wherein the third bore intersects the first bore comprising:
a locking roller axially displaceable in the third bore,
a resilient structure which exerts a force on the locking roller in the direction of the intersection of the first bore and the third bore, and
a fastener unit at the proximal end of the third bore;
wherein the device grasps and locks the cable through movement trajectories between the cable and the locking roller forming a pointed angle, leading to a movement of the locking roller relative to the housing, wherein the locking roller moves together with the cable along its length-axis and against its cross-axis.

42. The device of claim 41, further comprising an adapter in contact with the locking roller at a distal end of the adapter and the resilient structure at a proximal end of the adapter.

43. The device of claim 41, wherein the locking roller comprises a ball.

44. The device of claim 41, wherein the locking roller comprises a rounded cylinder.

45. The device of claim 41, wherein the resilient structure comprises a spring.

46. The device of claim 41, wherein the fastener unit comprises a laser-welded block.

47. The device of claim 41, wherein the fastener unit comprises a removable screw.

48. The device of claim 41, wherein the predetermined angulation of the third bore to the length axis of the housing is greater than 0° to about 20°.

49. The device of claim 48, wherein the predetermined angulation of the third bore to the length axis of the housing is about 10°.

50. The device of claim 41, wherein movement of the locking roller together with the cable allows for self-retaining grasping and locking of the cable.

51. The device of claim 50, wherein friction between the locking roller, the cable and the housing grasps and locks the cable without radial deflection of the cable.

52. The device of claim 51, wherein the cable is actively unlocked through introduction of a force onto the locking roller in a proximal direction.

53. The device of claim 52, wherein the force is initiated by the tappet, wherein the tappet pushes the locking roller against the resilient structure in a proximal direction.

54. The device of claim 50, wherein the locking roller is in contact with the cable and in contact with the tappet to allow for a controlled dragging and deceleration of the cable when the cable is moved from a proximal to a distal direction.

55. The device of claim 50, wherein the locking roller is in contact with the cable and in contact with the tappet to maintain a tensile force on the cable between 0 N to about the maximum tensile force of the cable.

56. The device of claim 55, wherein the tensile force on the cable decreases over time.

57. The device of claim 50, wherein the locking roller introduces a constant contact force onto the cable, introduced through the resilient structure, to control the diameter of the cable when the cable is moved from a proximal to a distal direction.

58. The device of claim 41, wherein the amount of force exerted on the locking roller and the device by the cable is greater than 0 N to about the maximum tensile force of the cable.

59. The device of claim 41, wherein the cable has a diameter of up to 2.0 mm.

* * * * *